United States Patent [19]

Burns

[11] E Re. 29,093

[45] Reissued Dec. 28, 1976

[54] TABLETTING SPHERICAL DENTAL AMALGAM ALLOY

[75] Inventor: Charles Francis Burns, Lansdowne, Pa.

[73] Assignee: Pennwalt Corporation, Philadelphia, Pa.

[22] Filed: Apr. 12, 1976

[21] Appl. No.: 676,185

Related U.S. Patent Documents

Reissue of:

[64] Patent No.: 3,933,961
Issued: Jan. 20, 1976
Appl. No.: 532,438
Filed: Dec. 13, 1974

[52] U.S. Cl. ..... 264/111; 29/192 R; 29/192 CP; 29/420; 427/216; 427/217; 427/436

[51] Int. Cl.[2] ..... B22F 1/02; B22F 3/02

[58] Field of Search ... 264/111; 29/192 R, 192 CP; 75/169, .5 R; 427/216, 217, 436

[56] References Cited

UNITED STATES PATENTS

| | | | |
|---|---|---|---|
| 1,803,386 | 5/1931 | Fischer | 75/169 |
| 3,574,607 | 4/1971 | Merkl | 75/169 |

*Primary Examiner*—Willard E. Hoag
*Attorney, Agent, or Firm*—Robert G. Danehower

[57] ABSTRACT

A process is provided for tabletting spherical dental amalgam alloy. The process comprises treating the particles of spherical alloy by contacting them with a hydrochloric acid solution of cupric chloride, separating the acidic cupric chloride solution from the spherical alloy particles, washing the spherical alloy particles with water, drying the spherical alloy particles to remove residual water and then compacting the treated spherical alloy particles into a solid form such as a tablet.

5 Claims, No Drawings

TABLETTING SPHERICAL DENTAL AMALGAM ALLOY

Matter enclosed in heavy brackets [ ] appears in the original patent but forms no part of this reissue specification; matter printed in italics indicates the additions made by reissue.

BRIEF DESCRIPTION OF INVENTION

Dental amalgam alloy in spherical form is desired for its homogeneity of composition and for its low ratio of mercury to alloy required for amalgamation. The latter is due to the fact that a sphere represents the solid shape of least surface area, therefore less mercury is required to wet the surface of the spheres.

For convenience in handling and for accuracy of measurement dentists prefer to have their amalgam alloy in the form of a tablet which is generally cylindrical in shape and of uniform weight. The dentist then adds a predetermined amount of mercury to the alloy and it is then triturated in an amalgamator. Unfortunately for tabletting purposes spherical alloy particles are extremely difficult to compact. Even at pressures of 80 tons per square inch it is difficult to obtain spherical alloy tablets which do not thereafter break on handling and shipping.

I have now discovered a process for treating the spherical shaped alloy particles which permits them to be compacted into tablets at forces as low as 2 to 4 tons. My treatment process comprises first contacting the spherical alloy particles with a hydrochloric acid solution of cupric chloride for a time sufficient to react with the alloy surface and grow cubical crystals containing copper thereon. Thereafter, the spherical alloy particles are separated from the acidic cupric chloride solution, washed with water, dried and compacted into tablets. Tabletting is readily accomplished in a STOKES tabletting machine.

DETAILED DESCRIPTION OF INVENTION

Dental amalgam alloy is generally prepared from silver, tin, copper and zinc. As hereinafter used in the specification and claims, the term "dental amalgam alloys" refers to alloys of this composition. Dental alloy composition may vary in percent by weight from 50 to 75% silver, 20 to 30% tin, 2 to 20% copper and from 0 to 2% zinc. Until about 1966, dental amalgam alloy was supplied in the form of a lathe cut. Lathe cut alloy is of irregular size and shape and readily forms tablets when compacted by compression. On the other hand, atomized spheres of alloy lack this irregularity of shape which permits compacting at reasonable pressures.

One approach to the tabletting of spherical shaped alloy particles is to add special lubricants and/or binders to the alloy particles. For example, most powders before compaction are mixed with lubricants such as zinc stearate, stearic acid, or waxes. The lubricant is added primarily to reduce die friction and interparticle friction. Following compaction the lubricant must be removed. With spherical alloy particles, especially recent dental formulations, additives such as the above do not enhance tablettability.

Another approach has been to provide special treatments for the surface of the particles to produce irregularity. These are several classic treatments given to spherical alloy particles for the sole purpose of forming compacts, in general these consist of the following:

Pickling — Surface pickling with acid solutions e.g., sulfuric acid (40–90%) and water, generates an irregular surface on each sphere but interferes with the reaction of the alloy when combined with mercury to form the end product, dental amalgam;

Plating — Generally, plating baths consist of cyanide, pyrophosphate, or acid solutions requiring temperatures from 70° to 180° F and the application of an electric current for plating to occur. The extensive manipulation and handling leads to high costs;

Oxidation — Surface oxidation requires judicious heat treatments and occasionally, acid treatments, which may or may not contribute to the formation of a metal powder compact. In addition this process is extremely time consuming and also expensive;

Polymer Coating — This process entails a multiphase operation, and in most instances, tablets or compacts can not be formed. It is also very difficult to obtain uniform coatings on 25 micron diameter particles;

Boric Acid Solutions — This process involves those metal powders requiring sintering and repressing for high densification.

In addition to having the capability of being compacted into a tablet a satisfactory alloy for dentistry must be capable of being amalgamated with no more than about 55 percent mercury. Preferably the amount of mercury required will be about 50 percent by weight while a superior amalgam alloy will amalgamate with about 45 percent by weight mercury. This mercury ratio limits the amount of etching that can be done on the surface of an alloy merely to obtain tabletting capability at reasonable pressures.

In contrast to the elaborate treatment processes of the prior art, I have discovered a simple chemical process for treating the surface of spherical alloy particles which produces sufficient surface irregularity to enable the formation of tablets by compacting at reasonable pressures.

Spherical alloy particles vary in diameter from about 5 to about 60 microns with a mean diameter of about 25 microns. Generally about two-thirds of the particles have a diameter between 15 to 35 microns.

The surface of these spherical alloy particles prior to the treatment of my invention are essentially smooth and at a magnification of 10,000 × have a surface appearance which resembles that of the outer surface of an orange peel.

In accordance with my invention the spherical alloy particles are contacted with a hydrochloric acid solution of cupric chloride. The acid concentration can range from about 5 volume percent concentrated hydrochloric acid in water to about 30 volume percent concentrated hydrochloric acid in water. Preferably, the acid concentration will be about 10 volume percent concentrated hydrochloric acid in water. These hydrochloric acid concentrations are based on diluting concentrated hydrochloric acid containing about thirty seven percent by weight hydrogen chloride in water.

Concentrations of hydrochloric acid which are greater than 30 volume percent of concentrated acid give the alloy surface too much porosity so that an excessive amount of mercury will be required for amalgamation. For the same reasons if the spherical alloy particles are in contact with the acid solution of cupric chloride for too long a period excessive etching and excessive porosity of the alloy particles take place.

The concentration of cupric chloride measured as $CuCl_2 \cdot 2H_2O$ will range from about 1 gram per liter of acid to about 10 grams per liter of hydrochloric acid solution.

The spherical alloy particles are contacted with the hydrochloric acid solution of cupric chloride in any convenient manner to insure intimate contact of the solution with every particle. A simple manner of contacting the alloy particles with the solution of cupric chloride is to place the alloy particles in a container equipped with an agitator, cover the alloy particles with cupric chloride solution and agitate the mixture.

The spherical alloy particles can also be contacted with the acidic cupric chloride solution in a tower wherein the alloy particles can drop through the acid solution. In another aspect of the treatment the alloy particles can move through a treating tower either in concurrent or counter-current flow with the acid solution. This manner of contacting the particles with the acid solution lends itself to continuous processing.

The quantity of the hydrochloric acid solution of cupric chloride used in contacting the alloy is not critical. Sufficient acid solution must be used to cover the alloy particles. A satisfactory volume of solution is about 10 volumes of hydrochloric acid solution of cupric chloride per gram of alloy. Any amount greater than this can be used. Ambient temperature is suitable for the chemical treatment.

The time of contact of the hydrochloric acid solution of cupric chloride with the spherical alloy particles must be at least 10 minutes. Too long a contact time must be avoided as this leads to excessive etching of the alloy with an undesirable increase in porosity with a resulting increase in the mercury to alloy ratio required for amalgamation. In general, the time of contact will be from about ten minutes to about 40 minutes.

The effect of the contact of the hydrochloric acid solution of cupric chloride on the spherical alloy under optimum conditions is to grow cubical crystals containing copper on the surface of the alloy. These cubical crystals provide the necessary interlocking points on the alloy particle to permit compacting at reasonable pressures. These cubical crystals containing copper have been observed by electron microscope examination at magnifications of 10,000 ×. Chemical analysis by the microprobe technique shows that the cubical crystals are rich in copper.

After the spherical alloy particles have been in contact with the hydrochloric acid solution of cupric chloride for at least about 10 minutes the solution is separated from the alloy particles. This is conveniently and efficiently done by vacuum filtering although other means of separating solids from liquids such as by centrifuging or by settling are satisfactory.

The residual acidic cupric chloride solution is removed from the spherical alloy particles by washing with potable water. Water washing is continued until nearly all of the residual acid has been displaced. Generally, about three or more displacement water washes are required.

The water washed spherical alloy particles are then dried in any convenient way to remove residual water left on the particles by the washing step. This is conveniently done in a vacuum shell dryer or rotary vacuum dryer or even in dryers at atmospheric pressure. Drying temperatures are not critical and temperatures of about 80° to about 100° C. are used. Drying is continued until the moisture content is about 1% or less. Preferably the drying will be continued until the moisture content approaches atmospheric humidity conditions.

The dried powder is then compacted into solid shapes, preferably in the form of cylindrical tablets. This is accomplished by compacting in tabletting, briquetting, molding, pelletizing or other type of compacting machine. Conveniently, tabletting is accomplished in a STOKES tabletting machine producing tablets of about 0.25 inches diameter, about 0.07 inches thick and weighing about 0.4 grams.

After tabletting the tablets are analyzed for any signs of strain introduced by the compaction. Such strains will generally reveal themselves when the tablets are measured for their green strength which should be within the range of about 3 to about 5 kilograms. The green strength is the resistance to fracture when the tablet is subjected to compaction pressure on its edge. Green strength of about 2 to about 5 kilograms are desired for easy amalgamation.

If the tablets require stress relief this is conveniently done by heating the tablets in an oven at about 90° to about 100° C. for about 1 to 4 hours. An inert gas atmosphere such as nitrogen is used to minimize surface oxidation.

The best mode of practicing my invention will be apparent from a consideration of the following examples.

EXAMPLE 1

Twenty grams of spherical alloy particles were placed in a glass beaker. The alloys had the following composition: Silver — 59.5%, Tin — 27.1%, Copper — 14.3% and Zinc — 0.05%. One hundred milliliters of various hydrochloric acid-water-cupric chloride solutions were added to the beaker as shown in Table I. The alloy in solution was stirred for a period of ten minutes after which the acid solution was separated from the alloy particles by vacuum filtration on filter paper. Approximately 300 milliliters of water were then passed through the alloy particles to remove the residual hydrochloric acid-cupric chloride solution. Following the wash water, the spherical alloy particles were again placed in a beaker, stirred and heated to about 100° C. until the water was evaporated.

After cooling to room temperature, samples of the particles weighing about 0.389 grams were compressed in a cylindrical mold at 4 tons for less than one second. The force was removed and the cylindrical tablets were examined under 70 × magnification for continuity of surface. The ratio of mercury required for amalgamation was also determined.

TABLE I

Hydrochloric Acid - Cupric Chloride Treatment of Spherical Alloy Particles

| Water (cc) | Hydrochloric Acid (37% conc.) (cc) | Cupric Chloride . $2H_2O$ (grams) |
|---|---|---|
| 0 | 100 | 0.25 |
| 10 | 90 | 0.25 |
| 25 | 75 | 0.25 |
| 50 | 50 | 0.25 |
| 70 | 30 | 0.25 |
| 75 | 25 | 0.25 |
| 90 | 10 | 0.25 |

In the runs using hydrochloric acid at a volume ratio greater than 30% hydrochloric acid to 70% water the surfaces of the alloy particles were etched excessively so that even though tablets were obtained having satisfactory green strength, the amount of mercury required for amalgamation exceeded 55% and the tablets were deemed unsatisfactory for this reason. Volume ratios of hydrochloric acid from about 30% to about 10% produced satisfactory tablets.

EXAMPLE 2

Using a hydrochloric acid to water ratio of 10 volume percent, the cupric chloride dihydrate concentration was varied as shown in Table 2.

TABLE II

Concentration of Cupric Chloride Dihydrate in Spherical Alloy Tablets

| Water (cc) | Hydrochloric Acid (37% conc.) (cc) | $CuCl_2 . 2H_2O$ (grams) |
|---|---|---|
| 90 | 10 | 0.10 |
| 90 | 10 | 0.25 |
| 90 | 10 | 0.50 |
| 90 | 10 | 1.00 |
| 90 | 10 | 5.00 |
| 90 | 10 | 10.00 |

Satisfactory tablets were prepared after treatment with hydrochloric acid solutions having from about 0.1 gram to about 1 gram of $CuCl_2 \cdot 2H_2O$ per 100 milliliters of acid solution. At higher concentrations tablets could not be formed.

EXAMPLE 3

Following the procedure described in Example 1, the time of contact of a 10 volume hydrochloric acid (37% conc.) 90 volume water solution containing 0.25 grams of $CuCl_2H_2O$ was varied from ten minutes to 40 minutes. All of the tablets produced from the treated spherical alloy particles were satisfactory.

EXAMPLE 4

Spherical alloy particles having alloy compositions as set forth below were treated in the manner described in Example 1 and in all cases produced satisfactory tablets.

| Silver | Tin | Copper | Zinc |
|---|---|---|---|
| 59.4 | 27.1 | 14.3 | 0.05 |
| 59.7 | 26.6 | 14.3 | 0.05 |
| 59.2 | 26.9 | 14.1 | 0.05 |
| 59.1 | 26.5 | 13.9 | 0.01 |
| 59.4 | 27.6 | 12.9 | 0.01 |
| [71.7] | [25.2] | [2.1] | [1.0] |
| [71.1] | [25.8] | [1.4] | [0.6] |
| [71.5] | [26.5] | [2.0] | [0.2] |

I claim:

1. The process for treating spherical alloy particles to enable them to be tabletted in a compacting press comprising:

contacting spherical dental amalgam alloy particles *having a composition within the range of 59.1 to 59.7% silver, 26.5 to 27.6% tin, 12.9 to 14.3% copper and 0.01 to 0.05% zinc* with a hydrochloric acid solution of cupric chloride for a time sufficient to react with the alloy surface and grow cubical crystals containing copper thereon said hydrochloric acid ranging in concentration from about 10 volume percent to about 30 volume percent concentrated hydrochloric acid and said cupric chloride ranging in concentration from about 0.1 grams to about 1 gram per 100 milliliters of hydrochloric acid solution;

separating the hydrochloric acid solution of cupric chloride from the spherical alloy particles;

washing the separated spherical alloy particles with water to remove the residual hydrochloric acid solution of cupric chloride;

drying the washed spherical alloy particles to remove residual water; and finally compacting the dried spherical alloy particles into a solid form.

2. The process of claim 1 in which the compacting is done by a tabletting machine.

[ 3. The process of claim 1 in which the spherical alloy particles are a silver, tin, copper and zinc alloy. ]

4. The process of claim 1 in which the hydrochloric acid solution of cupric chloride is in contact with the spherical alloy particles for a period ranging from about 10 minutes to about 40 minutes.

5. The process for treating spherical alloy particles to enable them to be tabletted in a compacting press comprising:

contacting spherical dental amalgam alloy particles *having a composition within the range of 59.1 to 59.7% silver, 26.5 to 27.6% tin, 12.9 to 14.3% copper and 0.01 to 0.05% zinc* with a hydrochloric acid solution of cupric chloride for a time sufficient to react with the alloy surface and grow crystals containing copper thereon said hydrochloric acid ranging in concentration from about 10 volume percent to about 30 volume percent concentrated hydrochloric acid and said cupric chloride ranging in concentration from about 0.1 grams to about 1 gram per 100 milliliters of hydrochloric acid solution;

separating the hydrochloric acid solution of cupric chloride from the spherical alloy particles;

washing the separated spherical alloy particles with water to remove the residual hydrochloric acid solution of cupric chloride; and drying the washed spherical alloy particles to remove residual water.

[ 6. The process of claim 5 in which the spherical alloy particles are a silver, tin, copper and zinc alloy. ]

7. The process of claim 5 in which the hydrochloric acid solution of cupric chloride is in contact with the spherical alloy particles for a period ranging from about 10 minutes to about 40 minutes.

* * * * *